United States Patent [19]
Lockerbie et al.

[11] Patent Number: 5,821,125
[45] Date of Patent: Oct. 13, 1998

[54] MONOCLONAL ANTIBODY SPECIFIC FOR NOVEL PKA BINDING PROTEINS

[75] Inventors: Robert Owen Lockerbie, Murray, Utah; W. Michael Gallatin, Mercer Island, Wash.

[73] Assignee: ICOS Corporation, Bothell, Wash.

[21] Appl. No.: 865,422

[22] Filed: May 29, 1997

Related U.S. Application Data

[63] Continuation of Ser. No. 682,265, Jul. 17, 1996, abandoned.

[60] Provisional application No. 60/001,043 Jul. 17, 1995.

[51] Int. Cl.$^6$ .............................. C12N 5/12; C07K 16/28; C12P 21/08
[52] U.S. Cl. .......................... 435/346; 435/326; 435/334; 530/358.1; 530/388.22; 530/387.2
[58] Field of Search ..................................... 435/346, 326, 435/334; 530/388.1, 388.22, 387.2

[56] References Cited

PUBLICATIONS

Coghlan et al 1995 Science 267:108.
Klauck et al 1996 Science 271:1589.
Allen et al., "Cyclosporin: A Therapy for Wegener's Granulomatosis" in *ANCA–Associated Vasculitides: Immunological and Clinical Aspects*, Gross (ed.) New York: Plenum Press (1993), pp. 473–476.
Belldegrun et al., "Interferon–α Primed Tumor–Infiltrating Lymphocytes Combined with Interleukin–2 and Interferon–α as Therapy for Metastatic Renal Cell Carcinoma", *J. Urol.* 150:1384–1390 (1993).
Bougneres et al., "Limited Duration of Remission of Insulin Dependency in Children with Recent Overt Type I Diabetes Treated with Low–Dose Cyclosporin", *Diabetes* 39:1264–1272 (1990).
Bregman et al., "Molecular Characterization of Bovine Brain P75, a High Affinity Binding Protein for the Regulatory Subunit of cAMP–dependent Protein Kinase IIβ*", *J.Biol.Chem.* 266:7207–7213 (1991).
Bruton and Koeller, "Recombinant Interleukin–2", *Pharmacotherapy* 14:635–656 (1994).
Brynskov, "Cyclosporin in Crohn's disease", *Dan.Med.Bull.* 41:332–344 (1994).
Carr et al., "Association of the type II cAMP–dependent Protein Kinase with a Human Thyroid RII–anchoring Protein", *J.Biol.Chem.* 267:13376–13382 (1992).
Carr et al., "Interaction of the Regulatory Subunit (RII) of cAMP–dependent Protein Kinase with RII–anchoring Proteins Occurs through an Amphipathic Helix Binding Motif*", *J.Biol.Chem.* 266:14188–14192 (1991).
Carr et al., "Localization of the cAMP–dependent Protein Kinase to the Postsynaptic Densities by A–Kinase Anchoring Proteins", *J.Biol.Chem.* 267:16816–16823 (1992).
Choi and Targan, "Immunomodulator Therapy in Inflammatory Bowel Disease", *Dig.Dis and Sci.* 39:1885–1892 (1994).

Coghlan et al., "Cloning and Characterization of AKAP 95, a Nuclear Protein That Associates with the Regulatory Subunit of Type II cAMP–dependent Protein Kinase*", *J.Biol.Chem.* 269:7658–7665 (1994).
Cooper et al., "Atopic Dermatitis: Recent Trends in Pathogenesis and Therapy", *J.Invest.Derm* 102:128–137 (1994).
Cuéllar et al., "Treatment of psoriatic arthritis", *Balliere's Clin.Rheum.* 8:483–498 (1994).
DeCamilli et al., "Heterogeneous Distribution of the cAMP Receptor Protein RII in the Nervous System: Evidence for Its Intracellular Accumulation of Microtubules, Microtubule–organizing Centers, and in the Area of the Golgi Complex", *J.Cell.Biol.* 103:189–203 (1986).
de Groen et al., "Central Nervous System Toxicity After Liver Transplantation", *N.Eng.J.Med.* 317:861–866 (1987).
Dillman, "The Clinical Experience with Interleukin–2 in Cancer Therapy", *Cancer Biotherapy* 9:183–209 (1994).
Dougados and Torley, "Efficacy of Cyclosporin A in Rheumatoid Arthritis: Worldwide Experience", *Br.J.Rheum* 32(suppl 1):57–59 (1993).
Eidelman et al., "Neurologic Complications of FK 506", *Transplnt.Proc.* 23:3175–3178 (1991).
Elliot and Chase, "Prevention or delay of Type 1 (insulin–dependent) diabetes mellitus in children using nicotinamide", *Diabetologia* 34:362–365 (1991).
Ellis et al., "Cyclosporine Improves Psoriasis in a Double–blind Study", *JAMA* 256:3110–3116 (1986).
Feldt–Rasmussen et al., "Oral cyclosporine for severe chronic idiopathic urticaria and angioedema", *Diabetes Medicine* 7:429–433 (1990).
Feutren, "Renal Morphology After Cyclosporin A Therapy in Rheumatoid Arthritis Patients", International Kidney Biopsy Registry of Cyclosporin (Sandimmum) in Autoimmune Diseases *Brit.J.Rheum.* 32(suppl 1):65–71 (1993).
Forre et al., "An Open, Controlled, Randomized Comparison Of Cyclosporine And Azathioprine In The Treatment Of Rheumatoid Arthritis: A Preliminary Report", *Arthritis Reheum.* 30:88–92 (1987).
Fradin et al., "Oral cyclosporine for severe chronic idiopathic urticaria and angioedema", *J.Am.Acad.Derm.* 25:1065–1067 (1991).
Fung et al., "Adverse Effects Associated With the Use of FK 506", *Transplant.Proc.* 23:3105–3108 (1991).
Glantz et al., "cAMP Signaling in Neurons: Patterns of Neuronal Expression and Intracellular Localization for a Novel Protein, AKAP 150, that Anchors the Regulatory Subunit of cAMP–Dependent Protein Kinase IIβ", *Mol. Cell.Biol.* 3:1215–1288 (1992).

(List continued on next page.)

*Primary Examiner*—Thomas M. Cunningham
*Assistant Examiner*—Martha T. Lubet
*Attorney, Agent, or Firm*—Marshall, O'Toole, Gerstein, Murray & Borun

[57] ABSTRACT

The present invention provides novel PKA-binding polypeptides, nucleic acids that encode the polypeptides and antibodies specifically immunoreactive with the polypeptides.

2 Claims, No Drawings

OTHER PUBLICATIONS

Glantz et al., "Characterization of Distinct Tethering and Intracellular Targeting Domain in AKAP75 a Protein That Links cAMP–dependent Protein Kinase IIβ to the Cytoskeleton*", *J.Biol.Chem.* 268:12796–12804 (1993).

Hafner et al., "Machanism of Inhibition of Raf–1 by Protein Kinase A," *Mol.Cell.Biol.* 14:6696–6703 (1994).

Haydon, et al., "New immunosuppressive treatment in transplantation medicine," Bailliere's Clinical Gastroenterology, vol. 8, pp. 445–464, (1994).

Hirsch et al., "Cloning and Expression of an Intron–less Gene for AKAP 75, an Anchor Protein for the Regulatory Subunit of cAMP–dependent Protein Kinase IIβ*", *J.Biol.Chem.* 267:2131–2134 (1992).

Hulton et al., "Long–term cyclosporin A treatment of minimal–change nephrotic syndrome of childhood", *Pediatr. Nephrol.* 8:401–403 (1994).

Jenner et al., "Cyclosporin A treatment of young children with newly–diagnosed Type 1 (insulin–dependent) diabetic mellitus", *Diabetiologia* 35:884–888 (1992).

Kahan, "Cyclosporine", *N.Eng.J.Med.* 321:1725–1738 (1989).

Kaplan, "Recent Advances in Cytokine Therapy in Leprosy", *J.Infect.Dis.* 167(suppl 1):s18–22 (1993).

Keryer et al., "A High–Affinity Binding Protein for the Regulatory Subunit of cAMP–Dependent Protein Kinase II in the Centrosome of Human Cells", *Exp.Cell Res.* 204:230–240 (1993).

Lange and Reiderer, "Glutamatergic Drugs in Parkinson's Disease", *Life Sciences* 55:2067–2075 (1994).

Leaker and Cairns, "Clinical aspects of cyclosporin nephrotoxicity", *Br.J.Hosp.Med.* 52:520–524 (1994).

Lockerbie et al., "Anchoring of protein kinase A is required for mediating the inhibitory effects of 3', 5'–cyclic adenosine monophosphate on IL–2 transcription in human T cells" *J.Cell Biochem.* Suppl.21A:76 Abstract D2155 (1995).

Ludwin and Alexopolulou, "Cyclosporin A Nephropathy in Patients with Rheumatoid Arthritis", *Br. J.Rheum.* 32(suppl 1):60–64 (1993).

MacFarlane et al., "The Hematologic Toxicity of Interleukin–2 in Patients with Metastatic Melanoma and Renal Cell Carcinoma", *Cancer* 75:1030–1037 (1995).

Manev et al., "Macrolide antibiotics protect neurons in culture against the N–methyl–D–aspartate (NMDA) receptor–mediated toxicity of glutamate", *Brain Res.* 624:331–335 (1993).

Martin et al., "Follow–up of cyclosporin A treatment in Type 1 (insulin–dependent) diabetes mellitus: lack of long–term effects", *Dibetologia* 34:429–434 (1991).

Mason, "Pharmacology of Cyclosporine (Sandimmune) VII. Pathophysiology and Toxicology of Cyclosporine in Humans and Animals", *Pharmacol.Rev.* 42:423–434 (1989).

McCartney et al., "Cloning and Characterization of A–kinase Anchor Protein 100(AKAP100)", *J.Biol. Chem.* 270:9327–9333 (1995).

Meldrum, "The role of glutamate in epilepsy and other CNS disorders", *Neurology* 44(suppl 8):S14–S23 (1994).

Merchant et al., "Immunotherapy for malignant glioma using human recombinant Interleukin–2 and activated autologous lymphocytes", *J.Neuro.* 8:173–188 (1990).

Meyrier, "Treatment of nephrotic syndrome with cyclosporin A. What remains in 1994?", *Nephrol.Dial. Transplant* 9:596–598 (1994).

Morris, "New Small Molecule Immunosuppressants for Transplantation: Review of Essential Concepts", *J.Heart and Lung Transplant.* (Nov./Dec) pp. S275–S285 (1993).

Olney, "Excitatory Transmitter Neurotoxicity", *Neurobiology of Aging* 15:259–260 (1994).

Pacor et al., "Cyclosporin in Behcet's Disease: Results in 16 Patients after 24 Months of Therapy", *Clin Rheum.* 13:224–227 (1994).

Pierce et al., "Cellular Therapy: Scientific Rationale and Clinical Results in the Treatment of Metastatic Renal–Cell Carcinoma", *Sem. Oncol.* 22:74–80 (1995).

Platz et al., "Nephrotoxicity Following Orthotopic Liver Transplantation", *Transplantation* 58:170–178 (1994).

Reece et al., "Neurologic complications in allogeneic bone marrow transplant patients receiving cyclosporin", *Bone Marrow Transplant.* 8:393–401 (1991).

Reitamo and Granlund, "Cyclosporin A in the treatment of chronic dermatitis of the hands", *Br.J.Derm.* 130:75–78 (1994).

Rios et al., "Identification of a high affinity binding protein for the regulatory subunit RIIβ of cAMP–dependent protein kinase in Golgi enriched membranes of human lymphoblasts", *EMBO J.* 11:1723–1731 (1992).

Rosenmund et al., "Anchoring of protein kinase A is required for modulation of AMPA/kainate receptors on hippocampal neurons", *Nature* 368:853–856 (1994).

Salek et al., "Cyclosporin greatly improves the quality of life of adults with severe atopic dermatitis. A randomized, double–blind, placebo–controlled trial", *Br.J.Derm.* 129:422–430 (1993).

Sánchez et al., "Immune Responsiveness and Lymphokine Production in Patients with Tuberculosis and Healthy Controls", *Inf.Immunol.* 62:5673–5678 (1994).

Schultz et al., "Cyclosporin A Therapy of Immune–Mediated Thrombocytopenia in Children" *Blood* 85:1406–1408 (1995).

Scott, "Cyclic Nucleotide–Dependent Protein Kinases" *Pharm.Ther.* 50:123–145 (1991).

Scott and McCartney, "Localization of A–kinase through Anchoring Proteins", *Mol.Endocrinol.* 8:5–11 (1994).

Sharma, et al., Which way for drug–mediated immunosuppression? *Curr.Opin.Immunol.* 6:784–790 (1994).

Shimizu et al., "Acute leucoencephalopathy during cyclosporin A therapy in a patient with nephrotic syndrome", *Pediatr.Nephrol.* 8:483–485 (1994).

Sturrock et al., "Acute haemodynamic and renal effects of cyclosporin and indomethacin in man", *Nephrol.Diag.Transplant* 9:1149–1156 (1994).

Svarstad et al., "Renal effects of maintenance low–dose cyclosporin A treatment in psoriasis", *Nephrol.Dial.Transplant* 9:1462–1467 (1994).

Thomason et al., "The Periodontal Problems and Management of the Renal Transplant Patient", *Renal Failure* 16:731–745 (1994).

Thomson and Starlz, "New Immunosuppressive Drugs: Mechanistic Insights and Potential Therapeutic Advances", *Immunol.Rev.* 136:71–98 (1993).

Threurkauf and Vallee, "Molecular Characterization of the c–AMP–dependent Protein Kinase Bound to Microtubule–associated Protein*," *J.Biol.Chem.* 257:3284–3290 (1992).

Tokuda et al., "Effect of Low–Dose Cyclosporin A on Systemic Lupus Erythematosus Disease Activity", *Arth.Rheumat.* 37:551–0558 (1994).

Towbin, "Electrophoretic transfer of proteins from polyacrylamide gels to nitrocellulose sheets: Procedure and some applications", *Proc.Natl.Acad.Sci.USA* 76: 4350–4354, (1979).

Van Joost et al., "Cyclosporin in atopic dermatitis" a multicentre placebo–controlled study, *Br.J.Derm.* 130:634–640 (1994).

Vogelzang et al., "Subcutaneous Interleukin–2 Plus Interferon Alfa–2a in Metastatic Renal Cancer: An Outpatient Multicenter Trial", *J.Clin.Oncol.* 11:1809–1816 (1993).

Vojtek et al., "Mammalian Ras Interacts Directly with the Serine/Threonine Kinase Raf", *Cell* 74:205–214 (1993).

Walsh et al., "An Adenosine 3', 5'–Monophosphate–dependent Protein Kinase from Rabbit Skeletal Muscle*", *J.Biol.Chem.* 243:3763–3765 (1969).

Wells and Tugwell, "Cyclosporin A in Rheumatoid Arthritis" Overview of Efficacy, *Br.J.Rheum.* 32(suppl 1):51–56 (1993).

Whittington et al., "Interleukin–2 A Review of its Pharmacological Properties and Therapeutic Use in Patients with Cancer", *Drugs* 46(3):447–515 (1993).

Wilson et al., "Sensorimotor neuropathy resembling CIDP in patients receiving FK506", *Muscle and Nerve* 17:528–532 (1994).

Young et al., "A prospective study of renal structure and function in psoriasis patients treated with cyclosporin", *Kidney International* 46:1216–1222 (1994).

MONOCLONAL ANTIBODY SPECIFIC FOR NOVEL PKA BINDING PROTEINS

This application is a continuation of application Ser. No. 08/682,265 filed Jul. 17, 1996, now abandoned and claims priority from Provisional Patent Application 60/001,043 filed on Jul. 17, 1995, now abandoned.

FIELD OF THE INVENTION

The present invention relates generally to proteins that bind protein kinase A within cells. More specifically, the present invention relates to novel proteins and nucleotide sequences encoding those proteins that localize protein kinase A within cells.

BACKGROUND OF THE INVENTION

Extracellular signals such as hormones and cytokines modulate many cellular activities by activating adenylate cyclase, increasing intracellular levels of cAMP and ultimately activating the cAMP-dependent kinase (PKA). PKA is a ubiquitous enzyme that functions in many intracellular pathways, for example, regulation of glycogen metabolism by reversible phosphorylation of glycogen phosphorylase [Walsh et al., *J. Biol. Chem.*, 243:3763–3765 (1969)], and regulation of MAP kinase signaling by inhibiting Raf-1 activation by Ras [Vojtek et al., *Cell*, 74:205–214 (1993) and Hafner et al., *Mol. Cell Biol.*, 14:6696–6703 (1994)]. Inactive PKA exists as a tetramer in which two identical catalytic subunits are bound to a dimer of two regulatory subunits. Activation of PKA by cAMP is effected by binding of a cAMP molecule to each of the regulatory subunits (R) causing release of the active catalytic subunit (C). While only one form of the C subunit has been identified, two classes of R subunit exist, RI and RII, with apparently distinct subcellular distributions. The RI isoforms (RIα and RIβ) are reported to be predominantly cytoplasmic and are excluded from the nucleus, whereas up to 75% of the RII isoforms (RIIα or RIIβ) are particulate and associated with either the plasma membrane, cytoskeletal components, secretory granules, golgi apparatuses, centrosomes or possibly nuclei [Scott, *Pharmac. Ther.*, 50:123–145 (1991)]. Presumably, differences (either physical or physiological) in the various R subunits provide a means by which cells are able to limit activity of the C subunit to a desired pathway.

Recent evidence indicates that cells are able to target PKA activity by localizing the inactive enzyme in the vicinity of potential substrates, thereby restricting the activity of the C subunit following release by cAMP binding to the R subunit. This "compartmentalization" segregates PKA with components in a given signaling pathway and contributes to PKA specificity in response to different extracellular stimuli. Compartmentalization of PKA occurs, at least in part, by interaction, or tethering, of the R subunit with specific proteins which localize, or anchor, the inactive holoenzyme at specific intracellular sites. Proteins which specifically segregate PKA have been designated A Kinase Anchor Proteins, or AKAPs [Hirsch et al., *J. Biol. Chem.*, 267:2131–2134 (1992)].

To date, a number of AKAPs have been identified [discussed below] which apparently bind PKA by a common carboxy terminal secondary structure motif that includes an amphipathic helix region [Scott and McCartney, *Mol. Endo.*, 8:5–11 (1994)]. Binding of PKA to most, if not all, identified AKAPs can be blocked in the presence of a peptide (Ht31) that mimics the common secondary helical structure, while a mutant Ht31 peptide, containing a single animo acid substitution that disrupts the helical nature of the peptide, has no effect on PKA/AKAP binding [Carr et al., *J. Biol Chem.*, 266:14188–14192 (1991)]. Even though PKA/AKAP interaction is effected by a common secondary structure, AKAPs (or homologous AKAPs found in different species) generally have unique primary structure as evidenced by the growing number of AKAPs that have been identified in a variety of organisms. Presumably, the unique amino acid structure, most notable in amino terminal regions of the proteins, accounts in part for AKAPs identified as unique to various specific cell types and for the various specific intracellular compartments in which PKA localization has been observed.

For example, AKAPs which are predominantly expressed in mammalian brain have been identified in rodents (AKAP 150) and cows (AKAP 75) [Bergman, et al., *J. Biol. Chem.* 266:7207–7213 (1991)], as well as a human protein (AKAP 79) [Carr, et al., *J. Bio. Chem.* 267:16816–16823 (1992)]. Amino acid identity and immunological cross-reactivity between these neuronal-specific proteins suggest that they represent interspecies homologs. As another example, AKAP 100 has been identified which appears to be specific for human and rat cardiac and skeletal muscle, while being expressed to a lower degree in brain cells of these mammals. As still another example, AKAP Ht31 [Carr et al., *J. Biol. Chem.*, 267:13376–13382 (1992)] has been identified and appears to be specific for thyroid cells. Conversely, AKAP 95 has been shown to be expressed in a multitude of cell types, showing no apparent tissue or cell-type specificity.

With regard to localization to specific intracellular compartments, AKAP 75, microtubule-associated protein (MAP-2) [Threurkauf and Vallee, *J. Biol. Chem.*, 257:3284–3290 (1982) and DeCamilli et al., *J. Cell Biol.*, 103:189–203 (1986)], AKAP 79 [Glantz et al., *J. Biol. Chem.*, 268:12796–12804 (1993)] and AKAP 150 [Glantz et al., *Mol. Biol. Cell*, 3:1215–1228 (1992)] are closely associated with cytoskeletal structural proteins, with AKAP 75 more specifically associated with post synaptic densities [Carr et al., *J. Biol. Chem.*, 267:16816–16823 (1992)]. Still other AKAPs have been shown to localize with less widespread cellular structures, including AKAP 350 association with centrosomes [Keryer et al., *Exp. Cell Res.*, 204:230–240 (1993)], AKAP 100 with the sarcoplasmic reticulum in rat cardiac tissue [McCartney, et al., *J. Biol. Chem.* 270:9327–9333 (1995)], an 85 kDa AKAP which links PKA to the Golgi apparatus [Rios et al., *EMBO J.*, 11:1723–1731 (1992)] and an unnamed AKAP that associates with membrane calcium channels.

Uniquely, AKAP 95, with an apparent zinc finger DNA-binding region, appears to reside exclusively in the nucleus [Coghlan et al., *J. Biol. Chem.*, 269:7658–7665 (1994)]. The DNA binding domain of AKAP 95 provides a role for direct involvement of PKA in specific gene transcription, possibly by positioning of PKA for phosphorylation of transcription factors. Other diverse cellular activities shown to be influenced by AKAP/PKA binding have been demonstrated by disruption of the interaction, for example, disruption of PKA/AKAP binding in T cells has been shown to reverse cAMP-induced suppression of interleukin 2 expression [Lockerbie et al., *J. Cell Biochem.*, Suppl. 21A:76, Abstract D2155 (1995)] and disruption of PKA/AKAP binding in hippocampal neurons has been shown to attenuate whole cell currents through alpha-amino-3-hydroxy-5-methyl-4-isoxazole propionic acid/kainate glutamate receptors [Rosenmund et al., supra.]. The ability of AKAPs to regulate IL-2 expression and to regulate glutamate receptor activity, in combination with a previous demonstration that AKAPs can bind calcineurin, suggest multiple therapeutic applications for AKAPs and molecules which modulate AKAP binding to cellular components.

In view of the diversity, both in terms of cell type expression, subcellular localization and physiological activities of AKAPs identified to date, there thus exists a need in the art to continue to identify novel AKAPs and nucleic acids which encode them. The uniqueness of AKAP primary structures provides a target for specifically regulating PKA localization, and thereby its function in specific cellular processes.

BRIEF SUMMARY OF THE INVENTION

In one aspect, the present invention encompasses antibodies specifically immunoreactive with a previously unidentified AKAP molecule. A presently preferred antibody is exemplified by the monoclonal antibody secreted by a hybridoma designated 160C and deposited with the American Type Culture Collection, 10801 University Boulevard, Manassas, Va. 20110-2209 on Jul. 19, 1995, and assigned Accession Number HB 11955. Other antibodies of the invention include polyclonal antibodies, recombinant antibodies and binding fragments of the same. Cell lines, e.g., hybridomas or cell lines transformed with recombinant expression constructs, which produce antibodies of the invention are also contemplated.

In another aspect, the present invention encompasses antigens specifically recognized by the antibodies of the invention. A preferred antigen is designated AKAP 120. Antigens recognized by the antibodies of the invention can be identified by any of a number of immunological techniques well known in the art. For example, immunospecific antigens may be isolated by affinity chromatography wherein antibodies of the invention are conjugated to an immobilized resin and the antigen removed from a particular fluid. As another example, antibodies of the invention may be utilized in immunoprecipitation procedures to specifically remove an antigen from a mixture of proteins and the immunoprecipitated protein subjected to further resolution using electrophoresis. As still another example, Western Blotting procedures may be employed with antibodies of the invention to identify specifically immunoreactive antigens in a mixture of proteins.

Also contemplated by the invention are polynucleotides encoding antigens recognized by antibodies of the invention. Polynucleotides of the invention include DNA (genomic, complementary, and synthetic) and RNA. Sense and anti-sense polynucleotides, complementary to coding and non-coding polynucleotides, respectively, are also comprehended. Polynucleotides of the invention are identified by any of a number of techniques well known in the art. For example, once the amino acid sequence of an immunospecific antigen is determined, degenerate or non-degenerate oligonucleotide probes can be synthesized to hybridize with an antigen-encoding clone in a library of DNA sequences. Alternatively, similar or unique oligonucleotide sequences can also be utilized in polymerase chain reaction (PCR) to amplify potential antigen-encoding clones from a mixture of polynucleotides. Polynucleotides of the invention include DNA encoding AKAP 120, as well as polynucleotides which hybridize under stringent conditions to DNA encoding AKAP 120. Those of ordinary skill in the art will understand hybridization conditions described as stringent.

The utility of the present invention is manifest. For example, antibodies of the invention are particularly useful for large scale purification of antigen specifically recognized by the antibodies. In addition, cell types which express antigens of the invention can be identified. Antibodies of the invention are also potentially useful as modulators of binding activity of the antigens specifically recognized, either via competitive binding inhibition by blocking amino acid sequences required for protein/protein interaction, or by inducing conformational changes in the antigen which result in distortion or elimination of a secondary structure required for protein binding.

Antigens specifically recognized by antibodies of the invention are useful in numerous applications. For example, antigens can be utilized to generate additional antibodies which may possess modulating activity. Antigens are also useful for permitting identification of polynucleotides which encode them. Antigens are also useful in screening procedures wherein modulators of antigen binding to other cellular components, e.g., other cellular proteins or cellular organelles, may be identified. Modulators so identified may potentially be utilized to regulate any of the numerous cellular activities in which antigens, or their binding partners, participate.

Polynucleotides of the invention are particularly useful for recombinant production of the antigens they encode. Recombinant expression permits large scale production of the antigens whose utility is addressed above. Polynucleotides are also useful for screening, for example, by di-hybrid screening technology, for genes which encode proteins that interact with the encoded antigen. Modulators of antigen binding can also be identified by screening methodologies, for example, tri-hybrid screening techniques using polynucleotides of the invention, to identify genes which encode proteins that modulate antigen binding. Modulators of AKAP binding are particularly useful in numerous applications. For example, small molecules may be found to inhibit either PKA/AKAP binding or AKAP interaction with specific cellular components. Compounds of this type would delocalize specific pools of PKA and affect only a targeted signaling pathway. Identification of modulators of AKAP binding to other cellular components may be equally beneficial. For example, factors which affect calcineurin activity in a manner similar to previously identified immunosuppressants, but have fewer side effects, may be useful in treatment of conditions now treated with more toxic immunosuppressants. In addition, identification of factors which modulate AKAP participation in cellular activities may also be useful in replacing currently accepted therapeutic intervention. For example, factors which regulate AKAP regulation of IL-2 expression may be useful in replacing administration of exogenous, recombinant IL-2.

DETAILED DESCRIPTION OF THE INVENTION

The following examples are offered by way of illustration and not of limitation. Example 1 describes generation of antibodies immunoreactive against T cell AKAPs. Example 2 relates to Western blot analysis of proteins recognized by the antibodies. Example 3 addresses affinity purification of a T cell AKAP recognized by the antibodies. Example 4 describes therapeutic applications of AKAPs and compounds that modulate AKAP binding.

EXAMPLE 1

Production of Anti-AKAP Antibodies

A. Polyclonal Antisera

A polyclonal serum was generated from mice immunized with recombinant AKAP 79 as described below.

Briefly, Balb/c mice, six to eight weeks old, were initially immunized with 50 µg each recombinant AKAP 79 in Freund's Complete Adjuvant. The AKAP 79 immunogen was expressed in *E. coli* as a fusion protein with a polyhistidine tail [(Carr, et al., *J. Biol. Chem.* 266:14188–14192 (1991)]. Four subsequent immunizations were administered at two to three week intervals, each with 50 µg AKAP 79 in Freund's Incomplete Adjuvant. A polyclonal serum was obtained following the final immunization which was shown by ELISA to recognize AKAP 79.

B. Monoclonal Antibodies

Monoclonal antibodies were generated using the immunization protocol described above for production of polyclonal serum. Following the final immunization, spleens were removed from the mice and fusions carried out as described below.

A single cell suspension was formed by grinding the spleen between frosted ends of two glass microscope slides submerged in serum-free RPMI 1640 media supplemented with 2 mM L-glutamine, 1 mM sodium pyruvate, 100 units/ml penicillin and 100 mg/ml streptomycin (Gibco, Canada). The cell suspension was filtered through a sterile 70-mesh Nirex cell strainer (Becton Dickinson, Parsippany, N.J.) and the cells were washed twice by centrifugation at 200× g for five minutes before being resuspended in 20 ml RPMI media. Thymocytes taken from three naive Balb/c mice were prepared in a similar manner.

NS-1 myeloma cells were kept in log phase with RPMI with 10% fetal bovine serum, (FBS) (HyClone Laboratories, Inc. Logan, Utah) for three days prior to fusion. Just prior to fusion, the cells were centrifuged at 200× g for five minutes, and the resulting pellet washed twice as described above. After washing, the cell suspension was brought to a final volume of 10 ml in serum free RPMI, and 10 µl was diluted 1:100. Approximately 20 µl of each dilution was removed, mixed with 20 µl 0.4% trypan blue stain in 0.85% saline (Gibco), loaded onto a hemacytometer (Baxter Healthcare Corp., Deerfield, Ill.) and viable cells counted.

Approximately $1.7 \times 10^8$ spleen cells were combined with $3.4 \times 10^7$ NS-1 cells, the mixture centrifuged and resulting supernatant discarded. The cell pellet was dislodged by tapping the tube and two ml of 37° C. PEG 1500 (50% in 75 mM Hepes, pH 8.0) (Boehringer Mannheim) was added over a one minute time period with stirring, followed by addition of 14 ml serum free RPMI over a seven minute time period. An additional 16 ml RPMI was added and the cells were centrifuged at 200× g for two minutes. After discarding the supernatant, the cell pellet was resuspended in 200 ml RPMI containing 15% FBS, 100 mM sodium hypoxanthine, 0.4 mM aminopterin, 16 mM thymidine (HAT) (Gibco), 25 units/ml IL-6 (Mallinckrodt) and $1.5 \times 10^6$ thymocytes/ml. The suspension was incubated for four hours at 37° C. before being dispensed into 10 96-well flat bottom tissue culture plates (Corning, United Kingdom) at 200 µl/well. Cells in plates were fed on days 3, 4, and 6 by aspirating approximately half of the medium from each well with an 18 G needle (Becton Dickinson) and replenishing plating medium described above, except containing 10 units/ml IL-6 and lacking thymocytes.

Fusion 160 was screened when cell growth reached 60–80% confluence (days 8–10 post-fusion) by ELISA. Immulon 4 plates (Dynatech, Cambridge, Mass.) were coated at 4° C. overnight with a 1:5000 dilution of unconjugated goat anti-mouse whole molecule (Cappel) in 50 mM carbonate buffer, pH 9.6. Plates were washed three times with PBS containing 0.05% Tween 20 (PBST) and 50 ml culture supernatant was added. After incubation for 30 minutes at 37° C. followed by washing as described above, 50 ml horseradish peroxidase-conjugated goat anti-mouse IgG(fc) (Jackson ImmnoResearch, West Grove, Pa.) diluted 1:3500 in PBST was added. Plates were covered with tape, incubated as described above, and washed three times with PBST. After the third wash, 100 µl substrate containing 1 mg/ml o-phenylene diamine (Sigma) and 0.1 ml/ml 30% $H_2O_2$ in 100 mM citrate buffer, pH 4.5, was added. The color reaction was stopped after six minutes with the addition of 50 µl 15% $H_2SO_4$. Absorbance at 490 nm was read on a plate reader (Dynatech) and wells showing reactivity were further tested for reactivity by dot blot analysis on AKAP 79. Two wells (designated 160C and 160K) were cloned two or three times successively by doubling dilution in RPMI, 15% FBS, 10 mM sodium hypoxanthine, 16 mM thymidine and 10 units/ml IL-6. Individual wells were scored visually after four days and the number of colonies in the less dense wells were recorded. Selected wells of each cloning were tested for reactivity with AKAP 79 by ELISA and dot blot analysis as described above. In the final cloning, positive wells containing single colonies were expanded in RPMI with 10% FBS. Monoclonal antibodies from the cloned cell lines were isotyped using an Isostrip isotyping kit (Boehringer Mannheim) according to manufacturer's recommended protocol.

Two monoclonal antibodies designated 160C and 160K were shown to be immunoreactive with AKAP 79 and of a IgG1 isotype.

EXAMPLE 2

Western Blotting

In order to determine the distribution of the antigen recognized by the polyclonal serum and the monoclonal antibodies identified in Example 1, Western blotting was performed using protein extract from various cell types.

Total cell extracts from cell types indicated below were prepared by boiling and sonicating cell pellets in 4% SDS, 200 mM DTT, 160 mM Tris-HCl, pH 6.8. Western Blots were performed according to standard protocol [Toubin, et al., *Proc. Natl. Acad. Sci.* (USA) 76:4350–4354 (1979)] PLEASE CORRECT THIS CITE FOR ME] including SDS-PAGE electrophoresis of 50–100 µg cell extract protein on 10% gels, protein transfer to a nitrocellulose membrane and blocking with 5% non-fat dry milk in Tris-buffered saline (TBS) containing 0.1% BSA. Following the blocking step, the membranes were incubated in TBS containing 5% BSA with primary and secondary antibodies; the secondary antibodies being goat anti-mouse IgG horse radish peroxidase conjugate (Boehringer Mannheim). Detection of immunoreactive protein bands was observed with enhanced chemiluminescence (ECL).

In Jurkat cell extract, the mouse polyclonal serum specifically recognized a 79 kD protein in addition to a protein of approximately 120 kD. In other cell extracts, the polyclonal serum recognized a 79 kD protein in a human kidney epithelial cell line (HEK 293) and in human brain, as well as known species homologs of AKAP 79, AKAP 75 from bovine brain and AKAP 150 from mouse brain.

Monoclonal antibody 160C recognized both the 120 kD protein in Jurkat extracts as well the human brain AKAP 79 but did not detect the 120 kD protein in total extracts of human neutrophils, promyelocytic HL60 cells, Ramos (B) cells, endothelial HUVEC cells, fibroblast COS cells or epithelial T84 cells. Antibody 160K, however, recognized only the brain AKAP 79 isoform.

In subsequent experiments, the 79 kD protein (as well as the 120 kD protein) was shown to bind RIIα using an RIIα overlay techniques, and is therefore likely to be a Jurkat T cell variant of human brain AKAP 79.

EXAMPLE 3

Affinity Purification of AKAP 120

In view of the fact that monoclonal antibody 160C was able to recognize a 120 kD protein in Jurkat cells, attempts were made to purify the 120 kD protein to determine it's relationship to AKAP 79.

A. cAMP-Sepharose chromatography

Approximately $1 \times 10^9$ Jurkat cells were grown in spinner flasks in RPMI complete medium. The cells were pelleted, washed three times in calcium-, magnesium-free phosphate buffered saline (CMF-PBS) and lysed (in 10 volumes of wet cell pellet weight) in Buffer A (20 mM Tris-HCl, pH 7.4, 1.5 mM $MgCl_2$, 1 mM DTT, 0.2 M NaCl, 0.1% NP-40 and a protease inhibitor cocktail) for 60 minutes at 4° C. The lysate was centrifuged at 40000× g for 30 minutes and the resulting supernatant applied to a 5 ml cAMP-Sepharose (Sigma) slurry previously equilibrated in Buffer A. The mixture was incubated for two hours at 4° C. before being transferred to a disposable BIORAD 10 ml column and washed with ten column volumes of Buffer A (without NP-40). The resin was then split equally; one half of the resin was incubated with three column volumes of 0.5 mM Ht31 peptide in Buffer A (without NP-40) and the other half incubated with three column volumes of 75 mM cAMP in Buffer A (without NP-40). Each incubation was carried out at room temperature for sixty minutes, after which the individual slurries were transferred to disposable 10 ml columns and the eluates collected. Protein in the eluate was concentrated greater than 10-fold using CENTRIPREP 10 (Amicon) columns prior to Western Blot analysis.

A protein of 120 kD was specifically eluted from cAMP-Sepharose by both the Ht31 amphipathic helix peptide and cAMP, which confirmed that the protein was an AKAP isoform and capable of binding the type II regulatory subunit (RII) of PKA.

B. Calmodulin-Agarose Chromatography

Cell lysates were prepared and processed as described in the above procedure, except that supernatant was applied to Calmodulin-Agarose (Sigma) resin previously equilibrated in Buffer A (described above) containing 0.5 mM $CaCl_2$ and no NP-40. Following transfer to a disposable column, the resin was washed in the same buffer and protein was eluted from the resin in Buffer A containing 2 mM EGTA, but no $CaCl_2$ or NP-40.

A 120 kD protein was specifically eluted from Calmodulin-Agarose, presumably either because of direct binding to calmodulin and/or indirect calmodulin binding through association with a complex of other calmodulin binding proteins, e.g. calcineurin.

EXAMPLE 4

Therapeutic Applications

The previous demonstration that AKAP 79 binds calcineurin is relevant in view of the fact that calcineurin is the target of two potent and clinically useful immunosuppressives, cyclosporin and FK506, both of which inhibit calcineurin activity. As described below, both cyclosporin and FK506 are useful in treatment of a variety of diseases, but have significant limiting side effects. Presumably, factors which modulate AKAP/calcineurin binding may ultimately modulate downstream signaling in this pathway, but perhaps with a greater cell type specificity that that observed by either cyclosporin or FK506. Identification of such a modulator, particularly with fewer side effects than those observed with other immunosuppressants, would possibly have widespread therapeutic use treatment of a multitude of disease currently treated with cyclosporin or FK506.

Numerous clinical indications of cyclosporin and FK506 have been reported. For example, cyclosporin has defined the standard for post-transplant immunosuppression, making possible liver, lung, intestine, and pancreas transplants, even though FK506 is generally believed to be a stronger immunosuppressive. Transplant patients who do not tolerate or fail on either cyclosporin or FK506 are sometimes successfully changed to the other drug.

As another example, inflammatory bowel disease (IBD) is a common term for two diseases having different clinical appearances, Crohn's disease and ulcerative colitis (UC). Cyclosporin has been successfully used to treat Crohn's disease, with statistically significant results of treatment having been demonstrated in at least one index of disease activity [Brynskov, Dan. Med. Bull. 41:332–344 (1994)]. Other indices, however, that correlate best with resolution of acute exacerbations showed non-significant trends toward improvement. Cyclosporin has also shown activity in severe acute steroid-resistant UC (the data are not significant as the trial was stopped for ethical reasons). Another trial of patients with sclerosing cholangitis and UC demonstrated borderline significance toward a milder course of UC. Relapse was common after withdrawal and treatment has been limited by concern for toxicity [Choi and Targan, Dig. Dis. and Sci. 39:1885–1892 (1994)]. In addition, other immunosuppressives have been used successfully in IBD, such as methotrexate, azathioprine, and 6-MP.

As another example, cyclosporin has been demonstrated to be effective in treating rheumatoid arthritis in several trials when used as a second or third line therapy of the disease, i.e., in patients that have failed other established therapies and have severe disease. In these trails, cyclosporin was found to be generally as effective and toxic as other second-line agents, such as gold, antimalarials, azathioprine, D-penicillamine, and methotrexate [Wells and Tugwell, Br. J. Rheum., 32(suppl 1):51–56 (1993); Forre et al., Arth. Rheum., 30:88–92 (1987)]. The trials only report treatment of "very severe, refractory active RA" because of cyclosporin's "potentially irreversible toxicity" [Dougados and Torley, Br. J. Rheum., 32(suppl 1):57–59 (1993)]. The renal toxicity is thought to have been primarily mediated through renal vasoconstriction that exacerbates NSAID nephrotoxicity and renal disease inherent in rheumatoid arthritis [Leaker and Cairns, Br. J. Hosp. Med., 52:520–534 (1994); Sturrock et al, Nephrol. Dial. Transplant, 9:1149–1156 (1994); Ludwin and Alexopolulou, Br. J. Rhewn., 32(suppl 1):60–64 (1993)]. About 10% of renal biopsies from RA patients treated with cyclosporin showed morphological features of cyclosporin toxicity [International Kidney Biopsy Registry of Cyclosporin in Autoimmune Diseases, Br. J. Rheum., 32(suppl 1):65–71 (1993)].

As still another example, cyclosporin has been reported to be effective for treatment of steroid-dependent asthma. In one trial, a small number of patients were randomized to cyclosporin or placebo, and the cyclosporin group exhibited increased airflow and FVC as well as fewer rescue courses of prednisolone.

As another example, cyclosporin was shown to be effective in the treatment of steroid-dependent minimal change disease nephrotic syndrome. Patients in this trail were shown to have lower steroid requirements on low dose cyclosporin, but all relapsed when cyclosporin was discontinued. Steroid-resistant forms of nephrotic syndrome have only a 20–30% response rate to cyclosporin [Meyrier, *Nephrol. Dial. Transplant,* 9:596–598 (1994); Hulton et al., *Pediatr. Nephrol.,* 8:401–403 (1994)].

With regard to treatment of systemic lupus erythematosus (SLE), one study reported significant decrease of SLE activity indices in a prospective non-randomized, non-controlled study [Tokuda et al., *Arthr. Rheumat.,* 37:551–558 (1994)]. Other studies, however, have not demonstrated efficacy in SLE.

As another example, cyclosporin has been shown to induce remission in insulin-dependent diabetes mellitus when instituted early after initial presentation. Remissions averaged about one year, although some were extended up to 850 days [Jenner et al., *Diabetologia,* 35:884–888 (1992); Bougneres et al., *Diabetes,* 39:1264–1272 (1990)]. No long-lasting effect of cyclosporin was noted in extended follow-up of one study [Martin et al., *Diabetologia,* 34:429–434 (1991)]. In another study, however, renal function deteriorated during treatment for 12–18 months and did not return completely to placebo level indicating that some chronic renal injury may have occurred [Feldt-Rasmussen et al., *Diabetes Medicine,* 7:429–433 (1990)]. Earlier intervention would be needed to enhance the effect of immunosuppressive therapy on the course of insulin-dependent diabetes mellitus. Some investigators are screening first degree relatives and successfully prophylactically treating those with diabetic markers [Elliott and Chase, *Diabetologia,* 34:362–365 (1991)].

As still another example, psoriasis has been effectively treated by cyclosporin [Cuellar et al., *Balliere's Clin. Rheum.,* 8:483–498 (1994); Ellis et al., *JAMA* 256:3110–3116 (1986)]. High dose therapy was effective for treatment of psoriatic arthritis, a particularly serve form of destructive arthritis, and discontinuation of therapy was generally followed by exacerbation of skin and joint disease. In view of the potential side effects and the need for continuous long term treatment, cyclosporin is only indicated for refractory psoriatic arthritis that is not adequately treated by other means.

In addition, cyclosporin has been demonstrated to be effective for treatment of severe atopic dermatitis in placebo-controlled and double-blinded studies [Van Joost et al, *Br. J. Derm.,* 130:634–640 (1994); Cooper, *J. Invest. Derm.,* 102:128–137 (1994)]. Side effects of nausea, abdominal discomfort, paresthesias, cholestasis, and renal insufficiency from the drug were preferred by patients to their untreated disease. Another randomized double-blind, placebo-controlled study found that cyclosporin treatment significantly increased the quality of life for patients with severe atopic dermatitis [Salek et al., *Br. J. Derm.,* 129:422–430 (1993)]. Skin lesions quickly relapsed following cessation of cyclosporin, but quality of life remained improved.

As still another example, cyclosporin has been used in treatment of chronic dermatitis of the hands, a disease with a reported prevalence of 4–22%, and typically treated with topical steroids to which many patients, however, do not respond. Low dose cyclosporin has been shown to effectively treated 5/7 patients in an open study [Reitamo and Granlund, *Br. J. Derm.,* 130:75–78 (1994)]. Approximately half of the patients relapsed after cyclosporin was discontinued.

As still another example, cyclosporin has been utilized in treatment of urticaria and angioedema, idiopathic skin diseases that present as hives and subcutaneous swelling. The pathology is related to mast cells, and treatment is often ineffective. IN one trail, three patients with refractory urticaria and angioedema were treated with cyclosporin and all symptoms resolved within one week [Fradin et al., *J. Am. Acad. Derm.,* 25:1065–1067 (1991)]. All patients had to stop therapy because of side effects, and symptoms recurred after therapy was discontinued.

With regard to other rheumatological diseases, studies report effective cyclosporin treatment of other less common autoimmune diseases, including Behcet's Disease [Pacor et al., *Clin. Rheum.,* 13:224–227 (1994)], Wegner's Granulomatosis [Allen et al., *Cyclosporin A Therapy for Wegner's Granulomatosis* in ANCA-Associated Vasculitides: Immunological and Clinical Aspects, Gross ed. Plenum Press (1993)], and immune-mediated thrombocytopenia [Schultz et al, *Blood* 85:1406–1408 (1995)].

In many of the trials described above, use of cyclosporin or FK506 was associated with many undesired side effects. In general, increased risk of infection and malignancy are associated with general immunosuppression, and it is unlikely that an AKAP-related immunosuppressive would not have similar risks. Other side effects may be avoided or reduced, however, by AKAP tissue specificity. The most common serious side effect of both cyclosporin and FK506 is nephrotoxicity, which at least to some degree is dose related and occurs in most patients, generally in the form of a decrease in the glomerular filtration rate during treatment. This side effect, however, is at least partially reversible when the drug is discontinued [Leaker and Cairns, supra]. Typically, progressive renal insufficiency does not develop, although more follow-up is needed for definitive evaluation. Chronic injury has also been observed in patients receiving low dose cyclosporin (3–4 mg/kg/d), about 40% of biopsies of these patients showed changes of interstitial fibrosis, tubular atrophy, and arteriolopathy [Svarstad et al., *Nephrol Dial. Transplant,* 9:1462–1467 (1994); Young et al., *Kidney International,* 46:1216–1222 (1994)]. Changes in endothelial cells were also apparent in histological sections [Kahan, *N. Engl. J. Med.,* 321:1725–1748 (1989)]. The nephrotoxicity was postulated to have resulted primarily due to arteriolar vasoconstriction and chronic low-grade ischemia [Leaker and Carins, supra], although the drugs were also shown to be directly toxic to tubular cells and vascular interstitial cells [Platz et al., *Transplantation,* 58:170–178 (1994)]. Some reports indicate that the incidence and severity of nephrotoxicity may be slightly higher with FK506 [Platz et al., supra].

Another reported significant toxicity of both cyclosporin and FK506 was neurotoxicity, with clinical manifestations including seizures, confusion, blindness, coma, headache, ataxia, Parkinson's syndrome, paresthesias, psychosis, focal deficits, akinetic mutism, tremors, neuropathy, and sleep disturbances [Shimizu et al., *Pediatr. Nephrol.,* 8:483–385 (1994); Wilson et al., *Muscle and Nerve,* 17:528–532 (1994); Reece et al., *Bone Marrow Transpl.,* 8:393–401 (1991); Eidelman et al, *Transpl. Proc.,* 23:3175–3178 (1991); de Groen et al., *N. Engl. J. Med.,* 317:861–566 (1987)]. Following liver transplantation, moderate to severe neurotoxicity has been shown to occur in 10–20% of patients treated with FK506 and 3–12% of patients treated with cyclosporin. Neurotoxicity has also been associated with serum lipid abnormalities and liver dysfunction.

Other side effects of cyclosporin and/or FK506 include hepatotoxicity, glucose intolerance, hypertension, hirsutism, gastrointestinal symptoms, venous thrombosis, pancreatitis, and gingival hyperplasia [Morris, *J. Heart Lung Transplant,* 12:S275–S286 (1993); Fung et al., *Transpl. Proc.,* 23:3105–3108 (1991); Mason, *Pharmacol. Rev.,* 42:423–434 (1989); Kahan, *N. Engl. J. Med.,* 321:1725–1738 (1989); Thomason et al., *Renal Failure,* 16:731–745 (1994)]. Therefore, in view of the widespread utilization of cyclosporin and FK506 and the inherent side effects of their use, development of alternative immunosuppressives could be extremely beneficial.

For example, it is possible that delocalization of calcineurin from a putative T cell AKAP might inhibit calcineurin activity in T cell activation, and thereby providing a T cell-specific immunosuppressive having the utility of cyclosporin or FK506, but fewer side effects. The previous observation that delocalization of PKA from a T cell AKAP enhanced IL-2 expression in stimulated cells indicated that AKAP-localized PKA in some way contributes to a regulatory role in IL-2 expression during T cell activation. T cell-specific delocalization of PKA may therefore provide a means for enhancing IL-2 secretion in vivo, thereby mimicking recombinant IL-2 administration and possibly reducing previously reported toxicity of IL-2 treatment as described below.

IL-2 has been approved for treatment of metastatic renal carcinoma and approximately 15–20% of patients with metastatic renal cell carcinoma or malignant melanoma respond to IL-2 therapy. Some of these responses are durable, lasting more than 66 months [Dillman, *Cancer Biotherapy,* 9:183–209 (1994); Whittington and Faulds, *Drugs* 46:446–514 (1993)]. While high dose bolus therapy has been associated with several severe side effects (as described below), low dose subcutaneous or continuous infusion therapy produced a modest response rate (12%) while reducing toxicity [Vogelzang et al., *J. Clin. Oncol.,* 11:1809–1816 (1993)].

IL-2 therapy (with and without interferon-a and other agents) has been investigated in the treatment of other malignancies. For example, sustained clinical responses, but no cures, have been obtained in direct application of IL-2 to tumor beds following glioma resection [Merchant et al., *J. Neuro.,* 8:173–188 (1990)]. In still other trails, limited efficacy has been reported in lymphoma [Dillman, supra], colorectal carcinoma [Whittington and Faulds, supra], limited AML [Bruton and Koeller, *Pharmacotherapy,* 14:635–656 (1994)], ovarian cancer and early bladder cancer [Whittington and Faulds, supra.]. The number of participants in each of these studies was too small to permit significant conclusions regarding effectiveness, however.

IL-2 has also been used in combination with adoptive immunotherapy, and been demonstrated to be effective for treatment of metastatic renal carcinoma [Pierce et al., *Sem. Oncol.,* 22:74–80 (1995); Belldegrun et al., *J. Urol.,* 150:1384–1390 (1993)]. In addition, IL-2 may also be effective for treatment of certain infectious diseases, by decreasing skin bacterial load and levels of antigen in patients with leprosy following by intradermal injection [Kaplan, *J. Infect. Dis.,* 167(suppl 1):S18–22 (1993)]. Also it has been observed that, as compared to PPD-positive healthy controls, lymphocytes from patients with tuberculosis produce lower levels of IL-2 [Sanchez et al., *Inf. Immun.,* 62:5673–5678 (1994)], suggesting that IL-2 therapy may be of value in treatment of mycobacterial infections.

Despite the potential therapeutic value of IL-2, the cytokine is also associated with significant toxicity [unless otherwise noted, sources are Whittington and Faulds, Dillman and Bruton and Koeller, supra]. The major treatment-limiting side effects is capillary leak syndrome. IL-2 administration increases vascular permeability causing interstitial and pulmonary edema, with patients developing hypotension with a substantial number requiring pressors. Vigorous fluid resuscitation can cause life-threatening pulmonary edema. Up to 20% of patients may require intubation and mechanical ventilation. High does bolus administration causes more severe leak than low dose or slow continuous infusions, and in some regiments, 100% of patients require ICU support during IL-2 treatment. Myocarditis, cardiomyopathies and cardiac arrhythmias have also been observed. Acute renal failure may occur as a result of the capillary leak syndrome-induced hypotension.

IL-2 can also cause severe diarrhea with electrolyte imbalances, cholestasis, thyroid abnormalities, and acute pancreatitis. Anemia requiring transfusions occurs in 15–20% of treated patients [MacFarlane et al, *Cancer* 75:1030–1037 (1995)]. Thrombocytopenia with hemorrhage can occur and coagulation pathway defects are common. Over 70% of patients experience changes in mental status, including paranoid delusions, hallucinations, loss of interest, sleep disturbances, and drowsiness. Coma, visual defects, transient ischemic attacks, and paresthesias have also been reported. These drawbacks associated with exogenous with exogenous IL-2 suggest that alternatives, wherein for example, endogenous IL-2 production can be modulated and thus eliminate the requirement for exogenous IL-2 treatment, should be explored as potential therapeutics.

In addition to providing possible means to identify immunosuppressive drugs and modulators of IL-2 production, identification of AKAPs makes regulation of other cellular activity possible in view of the diverse metabolic pathways in which AKAPs have been shown to participate. For example, AKAP 79 is important in regulation of glutamate receptor-regulated ion channels in the post-synaptic density of neurons, presumably via binding PKA, PKC, and calcineurin. PKA regulates activity of AMPA receptor-regulated channels, and delocalization or inhibition of PKA attenuates AMPA ion channel activity. PKC regulates activity of NMDA receptor-regulated channels, and calcineurin has been shown to desensitize the NMDA receptor to stimuli. These observations indicate that localized kinases (PKA and PKC) may regulate activity of glutamate receptors in neurons. Dephosphorylation by calcineurin is the counter-regulatory mechanism of the NMDA receptors. This model agrees physiologically with evidence of seizures induced by cyclosporin or FK506.

In addition, glutamate receptors have been implicated in many neurological diseases. Glutamate and other excitatory amino acids can produce excitotoxicity in neurons, and excessive stimulation of postsynaptic glutamate receptors has been shown to be toxic to the neurons, causing acute neuronal degeneration. Hypoxia (such as following stroke or cardiac arrest) and CNS trauma have been shown to cause a marked outpouring of glutamate into the extracellular space, which then interacts with glutamate receptors and triggers the excitotoxic casade. Anti-excitatory agents have been shown to protect against brain injury in animals models [Olney, *Neurobiology of Aging,* 15:259–260 (1994)]. Interestingly, NMDA antagonists are toxic to some types of neurons indicating that glutamate may inhibit other excitatory pathways in those cells. Macrolide antibodies, such as FK506, have also been shown to protect against NMDA, but not kainate, excitotoxicity in cultured neurons [Manev, et al, *Brain Res.,* 624:331–335 (1993)].

Glutamate has also been implicated in Parkinson's Disease. NMDA antagonists protect dopaminergic neurons in substantia nigra in monkeys exposed to MPTP, a chemical that induces Parkinson's syndrome in humans and other primates. Amantadine and memantine are NMDA antagonists and have been used in Europe to treat Parkinson's disease, however, both have been shown to cause psychosis in some patients. There is also some evidence that glutamatergic neurons may be hyperactive in Parkinson's disease and inhibition could decrease the motor symptom's of the disease [Lange and Riederer, *Life Sciences*, 55:2067–2075 (1994)].

Glutamate also plays a role in seizure disorders, participating in initiation, spread, and maintenance of seizure activity. NMDA and non-NMDA antagonists are potent anticonvulsants [Meldrum, *Neurology*, 44(suppl 8):S14–S23 (1994)]. AMPA receptors have also been implicated in ALS and a trial of a receptor antagonist is currently in progress.[49]

In view of the total of these observations, it is not surprising that numerous other immunosuppressants are in clinical trials. The following information regarding such trails was obtained from Haydon and Haynes, *Balliere's Clin. Gastroentero.*, 8:455–464 (1994); Thomason and Starzi, *Immunol. Rev.* 1993, 71–98 (1993); and Morris *J. Heart Lung Transplant.*, 12:S275–S286 (1993). For example, azaspirane is an SKB compound that suppresses graft cellular infiltrates and induction of IL-2R, and also abolishes IL-2 and IFN-γ production. Apparently azaspirane induces some type of suppressor cell and there is some evidence of synergistic effects with cyclosporin.

As another example, mycophenolate mofetial is a Syntex compound which inhibits purine synthesis and has a T and B cell-selective antiproliferative effect. It depletes antibodies. Mycophenolate mofetial may also deplete adhesion molecules from cell surfaces. While the drug apparently has low toxicity, it may cause leukopenia, and has been used to treat psoriasis for 20 years.

As another example, mizoribine in a Sumitomo compound which inhibits DNA synthesis. The mechanism of action is identical to mycophenolate.

As another example, brequinar is a DuPont-Merck compound which inhibits pyrimidine synthesis by blocking dihydoorate dehydrogenase. Full reports of clinical trials are awaited. The drug has been reported to act synergistically with cyclosporin, but can cause thrombocytopenia, dermatitis and mucositis.

As still another example, 15-Deoxyspergualin is a Nippon-Kayaku compound which predominantly affects monocytelmacrophage function, including inhibition of oxidative metabolism, lysosomal enzyme synthesis, IL-1 production, and cell surface expression of MHC class II antigens. It is 70–90% effective in refractory kidney rejection, but bone marrow toxicity may occur at higher doses.

As another example, leflunomide is a Hoechst compound which inhibits cytokine action, blocks T cell activation and antibody synthesis. It is not toxic to the kidneys or bone marrow.

As another example, rapamycin is a Wyeth-Ayerst compound that is related to FK506. It is a prodrug that must bind an immunophillin to be active and does not inhibit calcineurin or block T cell cytokine production. By an unknown mechanism, rapamycin blocks G1 to S transition.

Numerous modifications and variations in the invention as set forth in the above illustrative examples are expected to occur to those skilled in the art. Consequently only such limitations as appear in the appended claims should be placed on the invention.

What is claimed is:

1. A monoclonal antibody secreted by a hybridoma designated 160C having the A.T.C.C. Accession No. HB 11955.

2. A hybridoma designated 160C having the A.T.C.C. Accession No. HB 11955.

* * * * *

UNITED STATES PATENT AND TRADEMARK OFFICE
CERTIFICATE OF CORRECTION

PATENT NO. : 5,821,125
DATED : October 13, 1998
INVENTOR(S) : Lockerbie et al.

It is certified that error appears in the above-identified patent and that said Letters Patent is hereby corrected as shown below:

Pg. 1, Col. 2, Glantz et al.: Please delete "3:1215-1288", and insert - -3:1215-1228- -.

Pg. 2, Col. 2, Glantz et al.: Please delete "Targeting Domain", and insert - -Targeting Domains- -.

Col. 6, line 41: Please delete "Toubin", and insert - -Towbin- -.

Col. 6, line 43: Please delete "PLEASE CORRECT THIS CITE FOR ME]".

Col. 8, line 3: Please delete "that that observed", and insert - -than that- -.

Col. 8, line 40: Please delete "trails", and insert - -trials- -.

Col.8, lines 54 & 55: Please delete "Br.J. Rhewn", insert -- Br.J. Rheum --.

Col. 9, line 1: Please delete "trail", and insert - -trial- -.

Col. 10, line 5: Please delete " IN one trial", insert -- In one trail--.

Col. 10, line 45: Please delete "Leaker and Carins", and insert - -Leaker and Cairns- -.

Col. 10, line 56: Please delete "8:483-385", and insert - -8:483-485- -.

Col. 10, line 60: Please delete "317:861-566" and insert - -317:861-866- -.

Col. 11, line 43: Please delete "trails", and insert - -trials- -.

UNITED STATES PATENT AND TRADEMARK OFFICE
CERTIFICATE OF CORRECTION

PATENT NO. : 5,821,125

DATED : October 13, 1998

INVENTOR(S) : Lockerbie et al.

It is certified that error appears in the above-identified patent and that said Letters Patent is hereby corrected as shown below:

Col. 12, line 9: Please delete "High does", insert -- High dose --.

Col. 13, line 23: Please delete "trails", and insert - -trials- -.

Col. 14, line 12: Please delete "monocytelmacrophage", and insert - -monocyte/machrophage- -.

Signed and Sealed this

Twenty-fourth Day of October, 2000

Attest:

Attesting Officer

Q. TODD DICKINSON

Director of Patents and Trademarks